United States Patent
Humayan

(10) Patent No.: US 9,980,447 B2
(45) Date of Patent: May 29, 2018

(54) MELON VARIETY NUN 71504 MEM

(71) Applicant: Nunhems B.V., Nunhem (NL)

(72) Inventor: Hasib Humayan, Acampo, CA (US)

(73) Assignee: Nunhems B.V., Nunhem (NL)

( * ) Notice: Subject to any disclaimer, the term of this patent is extended or adjusted under 35 U.S.C. 154(b) by 0 days. days.

(21) Appl. No.: 15/353,073

(22) Filed: Nov. 16, 2016

(65) Prior Publication Data

US 2017/0064917 A1 Mar. 9, 2017

(51) Int. Cl.
*A01H 5/08* (2018.01)
(52) U.S. Cl.
CPC ..................................... *A01H 5/08* (2013.01)
(58) Field of Classification Search
None
See application file for complete search history.

(56) References Cited

FOREIGN PATENT DOCUMENTS

WO 2013182646 A1 12/2013
WO 2014076249 A1 5/2014

OTHER PUBLICATIONS

Vos, Pieter, et al., "AFLP: a new technique for DNA fingerprinting", Nucleic Acids Research, 1995, pp. 4407-4414, vol. 23:21.
US Department of Agriculture, Agricultural Marketing Service, "Objective Description of Variety Muskmelon/Cantaloupe (*Cucumis melo* L.)" http://www.ams.usda.gov/sites/default/files/media/38-Muskmelon-Cantaloupe.pdf.
UPOV, Guidelines for the Conduct of Tests for Distinctness, Uniformity and Stability, TG104/5 (Geneva, as last revised in 2014), http://www.upov.int/edocs/tgdocs/en/tg104.pdf.
Ren, Yan, et al., "Shoot regeneration and ploidy variation in tissue culture of honeydew melon (*Cucumis melo* L. inodorus)", In Vitro Cell.Dev.Biol.,—Plant, 2013, pp. 223-229, vol. 49, DOI 10.1007/511627-012-9482-8.
Colijn-Hooymans, C.M., et al., "Competence for regeneration of cucumber cotyledons is restricted to specific development stages", Plant Cell, Tissue and Organ Culture, 1994, pp. 211-217, vol. 39.
Dorais and Papadopoulos, "Greenhouse Tomato Fruit Quality", Horticultural Reviews, 2001, vol. 26.
Wijnker, Erik, et al., "Hybrid recreation by reverse breeding in *Arabidopsis thaliana*", Nature Protocols, 2014, pp. 761-772, vol. 9:4.
Parvathaneni, Krishna Rajiv, et al., "Fingerprinting in Cucumber and Melon (*Cucumis* spp.) Genotypes Using Morphological and ISSR Markers", J. Crop Sci. Biotech, 2011 (Mar.), pp. 39~43, vol. 14, No. 1, DOI No. 10.1007/s12892-010-0080-1.
Brotman, Y., et al., "Resistance gene homologues in melon are linked to genetic loci conferring disease and pest resistance", Theor Appl Genet, 2002, pp. 1055-1063, vol. 104, DOI 10.1007/s00122-001-0808-x.

*Primary Examiner* — Brent T Page

(57) ABSTRACT

The invention provides a new and distinct hybrid variety of melon, NUN 71504 MEM.

19 Claims, No Drawings

MELON VARIETY NUN 71504 MEM

FIELD OF THE INVENTION

The present invention relates to the field of plant breeding and, more specifically, to the development of melon variety NUN 71504 MEM, also referred to as "NUN 71504", "NUN 71504 F1", "NUN 71504 hybrid", or "71504 MEM" and parts thereof and seeds from which the variety can be grown. The invention further relates to vegetative reproductions of NUN 71504 MEM, methods for in vitro tissue culture of NUN 71504 MEM explants and also to phenotypic variants of NUN 71504 MEM. The invention further relates to methods of producing fruits of NUN 71504 MEM or of phenotypic variants of NUN 71504 MEM.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential. One crop species which has been subject to such breeding programs and is of particular value is the melon.

One crop species which has been subject to such breeding programs and is of particular value is the melon. It is a member of the Cucurbitacea family. The genus *Cucumis melo* originated in Africa. The plant is a large and sprawling annual, grown for its fruit. The fruit of most species of *Cucumis melo* is often coloured attractively, commonly red, orange or yellow. Melon can contain black seeds, which are considered undesirable for certain uses.

Many different melon cultivars have been produced, and melon breeding efforts have been underway in many parts of the world. Some breeding objectives include varying the color, texture and flavor of the fruit, and absence of seeds. Other objectives include disease or pest resistance, optimizing flesh thickness, yield, suitability to various climatic circumstances, solid content (% dry matter), and sugar content.

SUMMARY OF THE INVENTION

In one aspect of the invention, a seed of melon variety NUN 71504 MEM is provided, wherein a representative sample of said seed has been deposited under Accession Number NCIMB 43021. The melon seed of the invention may be provided as an essentially homogeneous population of melon seed. Therefore, seed of the invention may be defined as forming at least about 97% of the total seed, including at least about 98%, 99% or more of the seed. The population of melon seed may be particularly defined as being essentially free from other seed. The seed population may be separately grown to provide an essentially homogeneous population of melon plants according to the invention. Also encompassed are a plant grown from a seed of melon variety NUN 71504 MEM and a plant part thereof.

In another aspect the invention provides for a hybrid variety of *Cucumis melo* called NUN 71504 MEM. The invention also provides for a seed or a plurality of seeds of the new variety, a plant produced from growing the seed of the new variety NUN 71504 MEM, and a progeny of any of these. Especially, a progeny retaining all or all but one, two or three of the "distinguishing characteristics" or all or all but one, two or three of the "morphological and physiological characteristics" or essentially all physiological and morphological characteristics of NUN 71504 MEM referred to herein, are encompassed herein as well as methods for producing these.

In one aspect, such progeny have all the physiological and morphological characteristics of melon variety NUN 71504 MEM when grown under the same environmental conditions. In another aspect such progeny have all or all but one, two or three the physiological and morphological characteristics as listed in Table 1 and/or 2 as melon variety NUN 71504 MEM when measured under the same environmental conditions (i.e. evaluated at significance levels of 1%, 5% or 10% significance, which can also be expressed as a p value).

In another aspect a plant of the invention or said progeny plants has/have 3, 4, 5, 6, 7, 8, or more or all of the distinguishing characteristics: 1) average fruit length at edible maturity; 2) average fruit diameter at edible maturity; 3) typical fruit seed cavity shape at edible maturity; 4) average fruit seed cavity length at edible maturity; 5) typical mature fruit rind colour; 6) fruit type; and 7) average petiole length, in addition to 3, 4, 5, 6, 7, 8, or more, or all of the other (average) characteristics as listed in Table 1 and/or 2. NUN 71504 MEM is a honeydew melon suitable for the fresh market.

Further, a melon fruit produced on a plant grown from these seeds is provided.

In yet another embodiment of the invention, a plant having one, two or three physiological and/or morphological characteristics which are different from those of NUN 71504 MEM and which otherwise has all the physiological and morphological characteristics of NUN 71504 MEM as listed in Table 1 and/or 2, wherein a representative sample of seed of variety NUN 71504 MEM has been deposited under Accession Number NCIMB 43021, is provided.

Further, a vegetatively propagated plant of variety NUN 71504 MEM, or a part thereof, is provided having all or all but one, two or three of the morphological and physiological characteristics of NUN 71504 MEM when grown under the same environmental conditions.

Also a plant part derived from variety NUN 71504 MEM is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on NUN 71504 MEM, hypocotyl, cotyledon, a scion, a stock, a rootstock, a pistil, an anther, and a flower or a part thereof. Fruits are particularly important plant parts. In yet another aspect, a seed of NUN 71504 MEM is provided. In still another aspect, a seed growing or grown on a plant of NUN 71504 MEM are provided.

Definitions

"Melon" or "muskmelon" refers herein to plants of the species *Cucumis melo*, and fruits thereof.

"Cultivated melon" refers to plants of *Cucumis melo* i.e. varieties, breeding lines or cultivars of the species *C. melo* as well as crossbreds thereof, or crossbreds with other *Cucumis melo* species, or even with other Cucurbitacea species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Cucumis melo* and related species.

The terms "melon plant designated NUN 71504 MEM", "NUN 09015", "71504 MEM" or "variety designated 71504 MEM" are used interchangeably herein and refer to a melon plant of variety NUN 71504 MEM, representative seed of which having been deposited under Accession Number NCIMB 43021.

A "seed of NUN 71504 MEM" refers to an F1 hybrid seed represented by the deposit with Accession Number NCIMB 43021. It contains an embryo of NUN 71504 MEM, or a "F1 hybrid embryo". When said seed is planted, it grows into a plant of NUN 71504 MEM.

A "seed grown on NUN 71504 MEM" refers to a seed grown on a mature plant of NUN 71504 MEM or inside a fruit of NUN 71504 MEM. The "seed grown on NUN 71504 MEM" contains tissues and DNA of the maternal parent, NUN 71504 MEM. The "seed grown on NUN 71504 MEM" contains an F2 embryo. When said seed is planted, it grows into a first generation progeny plant of NUN 71504 MEM.

"Tissue culture" refers to a composition comprising isolated cells of the same or a different type or a collection of such cells organized into parts of a plant. Tissue culture of various tissues of melon and regeneration of plants therefrom is well known and widely published (see, e.g., see, e.g., Ren et al., In Vitro Cell. Dev. Biol.-Plant (2013) 49:223-229; Colijn-Hooymans (1994), Plant Cell, Tissue and Organ Culture 39: 211-217). Similarly, the skilled person is well-aware how to prepare a "cell culture".

"UPOV descriptors" are the plant variety descriptors described for melon in the "Guidelines for the Conduct of Tests for Distinctness, Uniformity and Stability, TG104/5 (Geneva, as last revised in 2014), as published by UPOV (International Union for the Protection of New Varieties and Plants, available on the world wide web at upov.int) and which can be downloaded from the world wide web at upov.int/under edocs/tgdocs/en/tg104.pdf and is herein incorporated by reference in its entirety.

"USDA descriptors" are the plant variety descriptors for (*Cucumis melo*) in the form titled "OBJECTIVE DESCRIPTION OF VARIETY—Muskmelon/Cantaloupe (*Cucumis melo* L.)" as published by the US Department of Agriculture, Agricultural Marketing Service, Plant Variety Protection Office, Beltsville, Md. 20705 and which can be downloaded from the world wide web at ams.usda.gov/under ams.usda.gov/sites/default/files/media/38-Muskmelon-Cantaloupe.pdf.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE.

As used herein, the term "plant" includes the whole plant or any part or derivative thereof, preferably having the same genetic makeup as the plant from which it is obtained, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a part of a leaf, pollen, an ovule, an ambryo, a petiole, a shoot or a part thereof, a stem or a part thereof, a root or a part thereof, a root tip, a cutting, a seed, a part of a seed, seedcoat or another maternal tissue which is part of a seed grown on NUN 71504 MEM, hypocotyl, cotyledon, a scion, a graft, a stock, a rootstock, a pistil, an anther, and a flower or a part, parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant.

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

"REFERENCE VARIETY" refers to the variety Crispy pear from company Nunhems B.V., which has been planted in a trial together with NUN 71504 MEM. USDA descriptors of NUN 71504 MEM were compared to the USDA descriptors of REFERENCE VARIETY.

"Internode" refers to a portion of a plant stem between nodes.

"Node" refers to the place on a plant stem where a leaf is attached.

"Rootstock" or "stock" refers to the plant selected for its roots, in particular for the resistance of the roots to diseases or stress (e.g. heat, cold, salinity etc.). Normally the quality of the fruit of the plant providing the rootstock is less important.

"Scion" refers to a part of the plant that is attached to the rootstock. This plant is selected for its stems, leaves, flowers, or fruits. The scion contains the desired genes to be duplicated in future production by the stock/scion plant and may produce the desired melon fruit.

"Stock/scion" plant refers to a melon plant comprising a rootstock from one plant grafted to a scion from another plant.

"Grafting" refers to attaching tissue from one plant to another plant so that the vascular tissues of the two tissues join together. Grafting may be done using methods known in the art like: 1) Tongue Approach/Approach Graft, 2) Hole insertion/Terminal/Top Insertion Graft, 3) One Cotyledon/Slant/Splice/Tube Graft and 4) Cleft/Side Insertion Graft.

A plant having "all the physiological and morphological characteristics" of a referred-to-plant means a plant having the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

For NUN 71504 MEM the distinguishing characteristics are 1) average fruit length at edible maturity; 2) average fruit diameter at edible maturity; 3) typical fruit seed cavity shape at edible maturity; 4) average fruit seed cavity length at edible maturity; 5) typical mature fruit rind colour; 6) fruit type; and 7) average petiole length.

In certain embodiments the plant of the invention has all the physiological and morphological characteristics, except for certain characteristics mentioned, e.g. the characteristic(s) derived from a converted or introduced gene or trait and/or except for the characteristics which differ, for example a Single Locus Conversion.

In one embodiment, the invention relates to a Single Locus Converted plant of NUN 71504 MEM.

Similarity between different plants is defined as the number of morphological and/or physiological characteristics (or the characteristics as listed in Table 1 and/or 2 that are the same between the two plants that are compared when grown under the same environmental conditions. Numerical characteristics are considered "the same" when the value for a numeric characteristic is evaluated at significance levels of 1%, 5% or 10% significance level, or at p≤0.05 using one way Analysis of variance (ANOVA), a standard methods known to the skilled person. Non-numerical or "type" characteristic are considered "the same" if identical or having the same value when scored for USDA and/or UPOV descriptors, if the plants are grown under the same conditions.

"Distinguishing characteristics" or "distinguishing morphological and/or physiological characteristics" refers herein the characteristics which are distinguishing between NUN 71504 MEM and other melon varieties, such as REFERENCE VARIETY, when grown under the same environmental conditions, especially the following characteristics: 1) average fruit length at edible maturity; 2) average fruit diameter at edible maturity; 3) typical fruit seed cavity shape at edible maturity; 4) average fruit seed cavity length at edible maturity; 5) typical mature fruit rind colour; 6) fruit type; and 7) average petiole length. In one aspect, the distinguishing characteristics further include at least one, two, three or more (or all) of the characteristics listed in Table 1 and/or 2. All numerical distinguishing characteristics are statistically significantly different at p≤0.05.

Thus, a melon plant "comprising the distinguishing characteristics of "NUN 71504 MEM" refers herein to a melon plant which does not differ significantly from NUN 71504 MEM in characteristics 1) to 5) above. In a further aspect the melon plant further does not differ significantly from NUN 71504 MEM in one or more, or all characteristics 6) to 10) as mentioned above. In yet a further aspect the melon plant further does not differ in all or all but one, two, three, four, five or six characteristics listed in Table 1 and/or 2. In still another aspect the melon plant does not differ in any of the distinguishing characteristics 1) to 10) listed above.

The physiological and/or morphological characteristics mentioned above are commonly evaluated at significance levels of 1%, 5% or 10% or evaluated at p≤0.05 using ANOVA, when measured under the same environmental conditions. For example, a progeny plant of NUN 71504 MEM may have one or more (or all) of the essential physiological and/or morphological characteristics of NUN 71504 MEM listed in Table 1 and/or 2, as determined at the 5% significance level when grown under the same environmental conditions.

As used herein, the term "variety", "cultivated melon" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, hypocotyl, cotyledon, a scion, a stock, a rootstock, a pistil, an anther, and a flower or a part thereof, etc. When a whole plant is regenerated by vegetative propagation, it is also referred to as a vegetative propagation.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Planting" or "planted" refers to seeding (direct sowing) or transplanting seedlings (plantlets) into a field by machine or hand.

"Yield" means the total weight of all melon fruits harvested per hectare of a particular line or variety. It is understood that "yield" expressed as weight of all melon fruits harvested per hectare can be obtained by multiplying the number of plants per hectare times the "yield per plant".

"Marketable yield" means the total weight of all marketable melon fruits, especially fruit that is not cracked, damaged or diseased, harvested per hectare of a particular line or variety.

Refractometer % of soluble solids is the percentage of soluble solids in fruit juice, as defined by the USDA. It is also expressed as °Brix and indicates sweetness. The majority of soluble solids in melon are mainly sugars present in the fruits of melon. Hence the correlation with sweetness. Brix can be measured using a Brix meter (also known as Refractometer).

As used herein, the terms "resistance" and "tolerance" are used interchangeably to describe plants that show no symptoms or significantly reduced symptoms to a specified biotic pest, pathogen, abiotic influence or environmental condition. These terms are also used to describe plants showing some symptoms but that are still able to produce marketable product with an acceptable yield.

"Locus" (plural loci) refers to the specific location, place or site of a DNA sequence on a chromosome, where, for example, a gene or genetic marker is found. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristics of a plant, cell or organism, which characteristics are the manifestation of gene expression.

"Haploid" refers to a cell or organism having one set of the two sets of chromosomes in a diploid.

"Diploid" refers to a cell or organism having two sets of chromosomes.

"Netted" skin or rind refers to the presence of reticulate markings called 'netting' on the skin. "Non-netted" or "absence of netting" refers to the fruits lacking such netting. "Ribbed" refers to grooves and raised parts, running approximately straight and parallel from (near) blossom end to (near) abscission end that are called 'ribs'. "Non-ribbed" or "absence of ribbing" refers to the fruits lacking such ribs.

"Cavity" or "seed cavity" is the center of the fruit containing the maternal tissues and seeds.

"Harvest maturity" is referred to as the stage at which a melon fruit is ripe or ready for harvest or the optimal time to harvest the fruit. In one embodiment, harvest maturity is the stage which allows proper completion of the normal ripening.

"Flavor" (or flavour) refers to the sensory impression of a food or other substance, especially a melon fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

"Aroma" refers to smell (or odor) characteristics of melon fruits or fruit parts (fruit flesh).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one melon line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to a plant derived from a plant designated NUN 71504 MEM. A progeny may be derived by regeneration of cell culture or tissue culture or parts of a plant designated NUN 71504 MEM or selfing of a plant designated NUN 71504 MEM or by producing seeds of a plant designated NUN 71504 MEM. In further embodiments, progeny may also encompass plants derived from crossing of at least one plant designated NUN 71504 MEM with another melon plant of the same or another variety or (breeding) line, or wild melon plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to melon plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a melon variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a melon plant by transformation. A plant comprising a transgene stably integrated into its genome is referred to as "transgenic plant".

"Linkage" refers to a phenomenon wherein alleles on the same chromosome tend to segregate together more often than expected by chance if their transmission was independent.

"Haploid" refers to a cell or organism having one set of the two sets of chromosomes in a diploid. "Diploid" refers to a cell or organism having two sets of chromosomes. "Polyploid" refers to a cell or organism having three or more complete sets of chromosomes. "Triploid" refers to a cell or organism having three sets of chromosomes. "Tetraploid" refers to a cell or organism having four sets of chromosomes.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

"Substantially equivalent" refers to a characteristic that, when compared, does not show a statistically significant difference (e.g., p=0.05) from the mean.

The term "mean" refers to the arithmetic mean of several measurements. The skilled person understands that the appearance of a plant depends to some extent on the growing conditions of said plant. Thus, the skilled person will know typical growing conditions for melons described herein. The mean, if not indicated otherwise within this application, refers to the arithmetic mean of measurements on at least 10 different, randomly selected plants of a variety or line.

DETAILED DESCRIPTION

The present invention relates to a *Cucumis melo* variety, referred to as NUN 71504 MEM, which—when compared to check variety REFERENCE VARIETY—has a 1) a lower average fruit length at edible maturity; 2) a higher average fruit diameter at edible maturity; 3) typical fruit seed cavity shape at edible maturity that is circular; 4) a lower average fruit seed cavity length at edible maturity; 5) typical mature fruit rind colour; 6) fruit type; and 7) a higher average petiole length. Also encompassed by the present invention are progeny plants having all but 1, 2, or 3 of the morphological and/physiological characteristics of NUN 71504 MEM and methods of producing plants in accordance with the present invention.

A melon plant of NUN 71504 MEM differs from the most similar comparison variety REFERENCE VARIETY in one or more characteristics (referred herein to as "distinguishing characteristics" or "distinguishing morphological and/or physiological characteristics" (or essential physiological and/or morphological characteristics) selected from: 1) average fruit length at edible maturity; 2) average fruit diameter at edible maturity; 3) typical fruit seed cavity shape at edible maturity; 4) average fruit seed cavity length at edible maturity; 5) typical mature fruit rind colour; 6) fruit type; and 7) average petiole length.

In another embodiment the plant of the invention is resistant to some pests and diseases: NUN 71504 MEM has high resistance to *Fusarium oxysporum* f.sp. *melonis* race 0 and race 2 as well as intermediate resistance to *Spaerotheca fuliginea* (*Podospaera xanthii*) (Powdery mildew) race 1 and race 2.

It is understood that "significant" differences refer to statistically significant differences, when comparing the characteristic between two plant lines or varieties when grown under the same conditions. Preferably at least about 10, 15, 20, 50 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10% or evaluated at p≤0.05 using ANOVA, when measured in plants grown under the same environmental conditions.

Thus, in one aspect, the invention provides a seed of the melon variety designated NUN 71504 MEM wherein a representative sample of seeds of said variety was deposited under the Budapest Treaty, with Accession number NCIMB 43021.

In another aspect, the invention provides for a melon plant of variety NUN 71504 MEM, a representative sample of seed from said variety has been deposited under the Budapest Treaty, with Accession number NCIMB 43021.

A seed of NUN 71504 MEM is obtainable by crossing the male parent of NUN 71504 MEM with the female parent of NUN 71504 MEM and harvesting the seeds produced on the female parent. The resultant NUN 71504 MEM seeds can be grown to produce NUN 71504 MEM plants. In one embodiment a seed or a plurality of seeds of NUN 71504 MEM are packaged into containers of any size or type (e.g., bags, cartons, cans, etc.). The seed may be disinfected, primed and/or treated with various compounds, such as seed coatings or crop protection compounds.

Also provided is a plant of melon variety NUN 71504 MEM, or a fruit or other plant part thereof, produced from a seed, wherein a representative sample of said seeds has been deposited under the Budapest Treaty, with Accession Number NCIMB 43021. Also included is a cell culture or tissue culture produced from such a plant.

In one embodiment the invention provides a melon plant regenerated from the tissue or cell culture of NUN 71504 MEM, wherein the plant has all or all but one, two or three of of the physiological and morphological characteristics of NUN 71504 MEM as listed in Table 1 and/or 2 when determined at the 5% significance level or evaluated at p≤0.05 using ANOVA. In another embodiment, the invention provides a melon plant regenerated from the tissue or cell culture of NUN 71504 MEM, wherein the plant has all or all but one, two or three of the physiological and morphological characteristics of NUN 71504 MEM when determined at the 5% significance level or evaluated at p≤0.05 using ANOVA.

A plants of NUN 71504 MEM can be produced by seeding directly in the soil (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the melon seed may be planted through a black plastic mulch. The dark plastic will absorb heat from the sun, warming the soil early. It will also help to conserve moisture during the growing season, controls weeds and makes harvesting easier and cleaner. Melon can also be grown entirely in greenhouses. See for example: M Domis, A P Papadopoulos (2002) Horticultural Reviews for cultivation, harvesting, handling and postharvest methods commonly used.

In other aspects, the invention provides for a fruit of melon variety NUN 71504 MEM, or a plant part, such as pollen, flowers, shoots or cuttings of variety NUN 71504 MEM or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Melon (unless indicated otherwise), when grown under the same environmental conditions): 1) average fruit length at edible maturity; 2) average fruit diameter at edible maturity; 3) typical fruit seed cavity shape at edible maturity; 4) average fruit seed cavity length at edible maturity; 5) typical mature fruit rind colour; 6) fruit type; and 7) average petiole length.

In still another aspect the invention provides a method of producing a melon plant, comprising crossing a plant of melon variety NUN 71504 MEM with a second melon plant one or more times, and selecting progeny from said crossing. In one embodiment of the invention, the first step in "crossing" comprises planting seeds of a first and a second parent melon plant, often in proximity so that pollination will occur for example, mediated by insect vectors. Alternatively, pollen can be transferred manually. Where the plant is self-pollinated, pollination may occur without the need for direct human intervention other than plant cultivation.

In yet another aspect the invention provides a method of producing a melon plant, comprising selfing a plant of melon variety NUN 71504 MEM one or more times, and selecting progeny from said selfing.

In other aspects, the invention provides for a progeny of variety NUN 71504 MEM such as progeny obtained by further breeding NUN 71504 MEM. Further breeding NUN 71504 MEM includes selfing NUN 71504 MEM one or more times and/or cross-pollinating NUN 71504 MEM with another melon plant or variety one or more times. In particular, the invention provides for progeny that retain all the essential morphological and physiological characteristics of NUN 71504 MEM or that retain one or more of the distinguishing characteristics of the melon type described further above and when grown under the same environmental conditions. In another aspect, the invention provides for a vegetative reproduction of the variety and a plant having all but 1, 2, or 3 of the physiological and morphological characteristics of NUN 71504 MEM (e.g. as listed in Table 1 and/or 2).

The morphological and/or physiological differences between a plant according to the invention, i.e. NUN 71504 MEM or progeny thereof, or a plant having all but 1, 2, or 3 of the physiological and morphological characteristics of NUN 71504 MEM (as listed in Table 1 and/or 2); and another known variety can easily be established by growing NUN 71504 MEM next to the other variety (in the same field, under the same environmental conditions), preferably in several locations which are suitable for said melon cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of *Solanum*.

The morphological and physiological characteristics (and the distinguishing characteristics) of NUN 71504 MEM are provided in the Examples, in Table 1 and/or 2. Encompassed herein is also a plant derivable from NUN 71504 MEM (e.g. by selfings and/or crossing and/or backcrossing with NUN 71504 MEM and/or progeny thereof) comprising all or all but one, two or three of the physiological and morphological characteristics of NUN 71504 MEM listed in Table 1 and/or 2 as determined at the 5% significance level or evaluated at $p \leq 0.05$ using ANOVA when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality, post-flesh firmness, and Brix can be measured using known methods. (Fruit) Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502. For melons, it is preferably combined with a 8 mm round tip, also available from QA Supplies under #2006061-8.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In a preferred embodiment, the invention provides for a melon fruit of variety NUN 71504 MEM, or a part of said fruit. In another embodiment, the invention provides for a container comprising or consisting of a plurality of harvested melon fruits or parts of fruits of NUN 71504 MEM, or fruits of progeny thereof, or fruits of a derived variety.

In yet a further embodiment, the invention provides for a method of producing a new melon plant. The method comprises crossing a plant of the invention NUN 71504 MEM, or a plant comprising all but 1, 2, or 3 of the morphological and physiological characteristics of NUN 71504 MEM (as listed in Table 1 and/or 2), or a progeny plant thereof, either as male or as female parent, with a second melon plant (or a wild relative of melon) one or more times, and/or selfing a melon plant according to the invention i.e. NUN 71504 MEM, or a progeny plant thereof, one or more times, and selecting progeny from said crossing and/or selfing. The second melon plant may for example be a line or variety of the species *Cucumis melo*, or other *Cucumis* species or even other Cucurbitacea species.

Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another melon plant (and/or with a wild relative of melon). Progeny may have all the physiological and morphological characteristics of melon variety NUN 71504 MEM when grown under the same environmental conditions and/or progeny may have (be selected for having) one or more of the distinguishing characteristics of melon of the invention. Using common breeding methods such as backcrossing or recurrent selection, one or more specific characteristics may be introduced into NUN 71504 MEM, to provide or a plant comprising all but 1, 2, or 3 or more of the morphological and physiological characteristics of NUN 71504 MEM (as listed in Table 1 and/or 2).

The invention provides for methods of producing plants which retain all the morphological and physiological characteristics of NUN 71504 MEM. The invention provides also for methods of producing a plant comprising all but 1, 2, or 3 or more of the morphological and physiological characteristics of NUN 71504 MEM (e.g. as listed in Table 1 and/or 2), but which are still genetically closely related to NUN 71504 MEM. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 71504 MEM if its DNA fingerprint is at least 80%, 90%, 95% or 98% identical to the fingerprint of NUN 71504 MEM. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39~43). The invention also provides a plant and a variety obtained by these methods. Plants may be produced by crossing and/or selfing, or alternatively, a plant may simply be identified and selected amongst NUN 71504 MEM plants, or progeny thereof, e.g. by identifying a variant within NUN 71504 MEM or progeny thereof (e.g. produced by selfing) which variant differs from NUN 71504 MEM in one, two or three of the morphological and/or physiological characteristics (e.g. in one, two or three distinguishing characteristics), e.g. those listed in Table 1 and/or 2 or others. In one embodiment the invention provides a melon plant having a Jaccard's Similarity index with NUN 71504 MEM of at least 0.8, e.g. at least 0.85, 0.9, 0.95, 0.98 or even at least 0.99.

The present invention also provides a melon seed and a plant produced by a process that comprises crossing a first parent melon plant with a second parent melon plant, wherein at least one of the first or second parent melon plants is a plant provided herein, such as from variety NUN 71504 MEM. In another embodiment of the invention, melon seed and plants produced by the process are first filial generation (F1) melon seed and plants produced by crossing a plant in accordance with the invention with another, distinct plant.

The present invention further contemplates plant parts of such an F1 melon plant, and methods of use thereof. Therefore, certain exemplary embodiments of the invention provide an F1 melon plant and seed thereof.

WO2013182646 which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of NUN 71504 MEM (i.e. is progeny of NUN 71504 MEM), because the seed coat is genetically identical to NUN 71504 MEM. In one embodiment, the present invention relates to a seed coat comprising maternal tissue of NUN 71504 MEM. In another embodiment the invention relates to a melon seed comprising a seed coat that comprises maternal tissue from NUN 71504 MEM.

By crossing and/or selfing also (one or more) single traits may be introduced into the variety of the invention i.e. NUN 71504 MEM (e.g., using backcrossing breeding schemes), while retaining the remaining morphological and physiological characteristics of NUN 71504 MEM and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 71504 MEM by breeding with NUN 71504 MEM.

Alternatively, a single trait converted plant or single locus converted plant may be produced by the following steps
a. obtaining a cell or tissue culture of cells of NUN 71504 MEM;
b. genetically transforming or mutating said cells;
c. growing the cells into a plant; and
d. optionally selecting a plant that contains the desired single locus conversion The skilled person is familiar with various techniques for genetically transforming a single locus in a plant cell, or mutating said cells.

Any pest or disease resistance genes may be introduced into a plant according to the invention, i.e. NUN 71504 MEM, progeny thereof or into a plant comprising all but 1, 2, or 3 or more of the morphological and physiological characteristics of NUN 71504 MEM (e.g. as listed in Table 1). Resistance to one or more of the following diseases or pests is preferably introduced into plants of the invention: Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f.sp. *melonis* (Fom) race 0, *Fusarium oxysporum* f.sp. *melonis* (Fom) race 1, *Fusarium oxysporum* f.sp. *melonis* (Fom) race 2, *Fusarium oxysporum* f.sp. *melonis* (Fom) race 1-2, *Fusarium* Wilt R2, Anthracnose, Cucumber Mosaic, Squash Mosaic, Root Knot (Nematode), Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and Melon Leafminer. Other resistance genes, against pathogenic viruses, fungi, bacteria, nematodes, insects or other pests may also be introduced.

Thus, invention also provides a method for developing a melon plant in a melon breeding program, using a melon plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 71504 MEM or progeny thereof, or a plant comprising all but 1, 2, or 3 or more of the morphological and physiological characteristics of NUN 71504 MEM (e.g. as listed in Table 1 and/or 2), with a different melon plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Brotman et al., Theor Appl Genet (2002) 104:1055-1063). For breeding methods in general see Principles of Plant Genetics and Breeding, 2007, George Acquaah, Blackwell Publishing, ISBN-13: 978-1-4051-3646-4.

The invention also provides a melon plant comprising at least a first set of the chromosomes of melon variety NUN 71504 MEM, a sample of seed of said variety having been deposited under Accession Number NCIMB 43021; optionally further comprising a single locus conversion, wherein said plant has essentially all of the morphological and physiological characteristics of the plant comprising at least a first set of the chromosomes of melon NUN 71504 MEM. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 71504 MEM may also be mutated (by e.g. irradiation, chemical mutagenesis, heat treatment, etc.) and mutated seeds or plants may be selected in order to change one or more characteristics of NUN 71504 MEM. Methods such as TILLING may be applied to melon populations in order to identify mutants. Similarly, NUN 71504 MEM may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 71504 MEM, or progeny thereof, by transforming NUN 71504 MEM or progeny thereof with a transgene that confers the desired trait, wherein the transformed plant retains all the phenotypic and/or morphological and/or physiological characteristics of NUN 71504 MEM or the progeny thereof and contains the desired trait.

The invention also provides a plant having one, two or three physiological and/or morphological characteristics which are different from those of NUN 71504 MEM and which otherwise has all the physiological and morphological characteristics of NUN 71504 MEM, wherein a representative sample of seed of variety NUN 71504 MEM has been deposited under Accession Number NCIMB 43021. In particular variants which differ from NUN 71504 MEM in none, one, two or three of the characteristics mentioned in Table 1 and/or 2 are encompassed.

In one aspect, the plant having one, two or three physiological and/or morphological characteristics which are different from those of NUN 71504 MEM and which otherwise has all the physiological and morphological characteristics of NUN 71504 MEM differs from NUN 71504 MEM in one, two or three of the distinguishing morphological and/or physiological characteristics selected from 1) average fruit length at edible maturity; 2) average fruit diameter at edible maturity; 3) typical fruit seed cavity shape at edible maturity; 4) average fruit seed cavity length at edible maturity; 5) typical mature fruit rind colour; 6) fruit type; and 7) average petiole length.

In another embodiment the plant having one, two or three physiological and/or morphological characteristics which are different from those of NUN 71504 MEM and which otherwise has all the physiological and morphological characteristics of NUN 71504 MEM may differ from NUN 71504 MEM in one, two or three morphological or physiological characteristic other than the "distinguishing morphological and/or physiological characteristics" (or essential physiological and/or morphological characteristics) of NUN 71504 MEM selected from: 1) average fruit length at edible maturity; 2) average fruit diameter at edible maturity; 3) typical fruit seed cavity shape at edible maturity; 4) average fruit seed cavity length at edible maturity; 5) typical mature fruit rind colour; 6) fruit type; and 7) average petiole length.

Melons according to the invention, such as the variety NUN 71504 MEM, or its progeny, or a plant having all physiological and/or morphological characteristics but one, two or three which are different from those of NUN 71504 MEM, can also be reproduced using vegetative reproduction methods. Therefore, the invention provides for a method of producing plants, or a part thereof, of variety NUN 71504 MEM, comprising vegetative propagation of variety NUN 71504 MEM. Vegetative propagation comprises regenerating a whole plant from a plant part of variety NUN 71504 MEM (or from its progeny or from or a plant having all physiological and/or morphological characteristics of NUN 71504 MEM but one, two or three, which are different), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 71504 MEM (or from its progeny or from or a plant having all but one, two or three physiological and/or morphological characteristics of NUN 71504 MEM, or a part thereof, having one or more distinguishing characteristics and/or all the morphological and physiological characteristics of NUN 71504 MEM (except for the characteristics differing), when grown under the same environmental conditions.

A parts of NUN 71504 MEM (or of its progeny or of a plant having all physiological and/or morphological characteristics but one, two or three which are different from those of NUN 71504 MEM) encompasses any cells, tissues, organs obtainable from the seedlings or plants, such as but not limited to: a melon fruit or a part thereof, a cutting, hypocotyl, cotyledon, seedcoat, pollen and the like. Such parts can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered melon fruit from NUN 71504 MEM or from progeny thereof, or from a derived variety, such as a plant having all but one, two or three physiological and/or morphological characteristics of NUN 71504 MEM.

In one aspect a haploid plant and/or a double haploid plant of NUN 71504 MEM, or a plant having all but one, two or three physiological and/or morphological characteristics of NUN 71504 MEM, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or double haploid plants derived from NUN 71504 MEM that, when combined, make a set of parents of NUN 71504 MEM are encompassed herein.

Using methods known in the art like "reverse breeding", it is possible to produce parental lines for a hybrid plant such as NUN 71504 MEM; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 71504 MEM) comprising the step of making double haploid cells from haploid cells from the plant of the invention (NUN 71504 MEM) or a seed of that plant; and optionally crossing these parental lines to produce and collect seeds. In another aspect, the invention relates to a combination of parental lines produced by this method. In still another aspect said combination of parental lines can be used to produce a seed or plant of NUN 71504 MEM when these parental lines are crossed. In still another aspect, the invention relates to a combination of parental lines from which a seed or plant having all physiological and/or of NUN 71504 MEM morphological characteristics but one, two or three which are different can be produced or in another aspect, wherein a seed or plant having the distinguishing characteristics 1)-5) or 1)-10) of NUN 71504 MEM, as herein defined, can be produced when grown under the same environmental conditions. In still another aspect, the invention relates to a combination of parental lines from which a seed or plant having all the characteristics of NUN 71504 MEM as defined in Table 1 and/or 2 when grown under the same conditions can be produced.

In another alternative aspect, the invention provides a method of introducing a single locus conversion or single trait conversion or a desired trait into NUN 71504 MEM comprising:
a. obtain a combination of a male and a female parental line of NUN 71504 MEM,
b. introduce a single locus conversion in at least one of the parents of step a;
c. crossing the converted parent with the other parent of step a to obtain seed of NUN 71504 MEM A combination of a male and a female parental line of NUN 71504 MEM can be generated by methods described herein, for example through reverse breeding.

Step b) of the above method—introduce a single locus conversion in at least one of the parents of step a—may be done through the following method:
i. obtaining a cell or tissue culture of cells of the parental line of NUN 71504 MEM;
ii. genetically transforming or mutating said cells;
iii. growing the cells into a plant; and
iv. optionally selecting plants that contain the single locus conversion, the single trait conversion or the desired trait.

The invention further relates to plants obtained by this method.

Step b) of the above method—introduce a single locus conversion in at least one of the parents of step a—may be done through the following method:
i. crossing the parental line of NUN 71504 MEM with a second melon plant comprising the single locus conversion, the single trait conversion or the desired trait;
ii. selecting F1 progeny plants that contain the single locus conversion, the single trait conversion or the desired trait;
iii. crossing said selected progeny plants of step ii with the parental line of step i, to produce a backcross progeny plant;
iv. selecting backcross progeny plants comprising the single locus conversion, the single trait conversion or the desired trait and otherwise all or all but one, two or three of the morphological and physiological characteristics the parental line of step i to produce selected backcross progeny plants; and
v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is pest resistance or disease resistance.

In one embodiment the trait is disease resistance and the resistance is conferred to Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f.sp. *melonis* (Fom) race 0, *Fusarium oxysporum* f.sp. *melonis* (Fom) race 1, *Fusarium oxysporum* f.sp. *melonis* (Fom) race 2, *Fusarium oxysporum* f.sp. *melonis* (Fom) race 1-2, *Fusarium* Wilt R2, Anthracnose, Cucumber Mosaic, Squash Mosaic, Root Knot (Nematode), Aphid, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer.

Also provided are plant parts derived from variety NUN 71504 MEM (or from its progeny or from a plant having all but one, two or three physiological and/or morphological characteristics which are different from those of NUN 71504 MEM, or from a vegetatively propagated plant of NUN 71504 MEM (or from its progeny or from a plant having all but one, two or three physiological and/or morphological characteristics which are different from those of NUN 71504 MEM), being selected from the group consisting of a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on NUN 71504 MEM, hypocotyl, cotyledon, a scion, a stock, a rootstock, a pistil, an anther, and a flower or a part thereof.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a melon fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

For example, containers such as cans, boxes, crates, bags, cartons, Modified Atmosphere Packagings, films (e.g. biodegradable films), etc. comprising a plant or a parts of a plant (fresh and/or processed) described herein or a seed of NUN 71504 MEM are also provided herein.

Marketable melon fruits are generally sorted by size and quality after harvest. Alternatively the melon fruits can be sorted by expected shelf life, pH or Brix.

Melons may also be grown for use in grafting or inosculation as rootstocks (stocks) or scions (cions). Typically, different types of melons are grafted to enhance disease resistance, which is usually conferred by the rootstock, while retaining the horticultural qualities usually conferred by the scion. It is not uncommon for grafting to occur between cultivated melon varieties and related *Solanum* species. Methods of grafting and vegetative propagation are well-known in the art.

So in one aspect the invention relates to a plant comprising a rootstock or scion of NUN 71504 MEM.

All documents (e.g., patent publications) are herein incorporated by reference in their entirety. Cited references:

EXAMPLES

Development of NUN 71504 MEM

The hybrid NUN 71504 MEM was developed from a male and female proprietary inbred line of Nunhems. The female and male parents were crossed to produce hybrid (F1) seeds of NUN 71504 MEM The seeds of NUN 71504 MEM can be grown to produce hybrid plants and parts thereof (e.g. melon fruit). The hybrid NUN 71504 MEM can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 71504 MEM is uniform and stable.

DEPOSIT INFORMATION

A total of 2500 seeds of the hybrid variety NUN 71504 MEM were deposited according to the Budapest Treaty by Nunhems B.V. on Apr. 5, 2018, at the NCIMB Ltd., Ferguson Building, Craibstone Estate, Bucksburn, Aberdeen AB21 9YA, United Kingdom (NCIMB). The deposit has been assigned NCIMB number 43021. A deposit of NUN 71504 MEM and of the male and female parent line is also maintained at Nunhems B.V. Access to the deposit will be available during the pendency of this application to persons determined by the Director of the U.S. Patent Office to be entitled thereto upon request. Subject to 37 C.F.R. § 1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 71504 MEM is referred to as REFERENCE VARIETY, a variety from Nunhems B.V. with the commercial name Crispy pear. In Table 1 a comparison between NUN 71504 MEM and REFERENCE VARIETY is shown based on a trial in the USA. Trial location: Acampo, Calif., USA; N38.192873 W121.232637. Transplanting date for NUN 71504 MEM: 17 Jun. 2016.

Two replications of 50 plants each, from which 15 plants or plant parts were randomly selected, were used to measure characteristics. In Table 1 the USDA descriptors of NUN 71504 MEM (this application) and reference Crispy Pear (commercial variety) are listed.

In accordance with one aspect of the present invention, there is provided a plant having the physiological and morphological characteristics of melon variety NUN 71504 MEM as presented in Table 1.

TABLE 1

| USDA Descriptor | Application Variety NUN 71504 MEM | Reference Variety Crispy pear |
|---|---|---|
| 1. TYPE:<br>1 = Persian 2 = Honey Dew 3 = Casaba<br>4 = Crenshaw 5 = Common/Summer<br>6 = Other | 2 | 6 |
| 2. AREA OF BEST ADAPTATION IN U.S.A.:<br>1 = Southeast 2 = Northeast/North Central<br>3 = Southwest 4 = Most Areas<br>5 = East coast | 3 | 3 |
| 3. MATURITY:<br>Days From Seeding to Harvest | 85 | 85 |
| 4. PLANT: | | |
| Fertility: 1 = Andromonoecious<br>2 = Monoecious 3 = Gynoecious<br>4 = Other | 1 | 1 |
| Habit:<br>1 = Vine 2 = Semi-bush 3 = Bush | 1 | 1 |
| 5. LEAF: | | |

TABLE 1-continued

| USDA Descriptor | Application Variety NUN 71504 MEM | Reference Variety Crispy pear |
|---|---|---|
| Shape: 1 = Orbicular 2 = Ovate 3 = Reniform (Cordate) | 3 | 3 |
| Lobes: 1 = Not Lobed 2 = Shallowly Lobed 3 = Deeply Lobed | 2 | 2 |
| Color: 1 = Light Green (Honey Dew) 2 = Medium Green 3 = Dark Green (Rio Gold) | 2 | 2 |
| Color Chart Code (RHS chart) | Green NN137A | Green 137A |
| Average Length mm | 134.2 | 129.2 |
| Average Width mm | 190.1 | 182.8 |
| Surface: 1 = Pubescent 2 = Glabrous 3 = Scabrous | 3 | 3 |
| 6. FRUIT: | | |
| Average Length in cm | 16.4 | 18.3 |
| Average Diameter in cm | 14.0 | 13.6 |
| Average Weight in gram | 1687.5 | 1805.3 |
| Shape: 1 = Oblate 2 = Oval 3 = Round 4 = Elongate-Cylindrical 5 = Spindle 6 = Acorn | 2 | 2 |
| Surface: 1 = Smooth 2 = Netted 3 = Corrugated 4 = Warted | 1 | 1 |
| Blossom Scar: 1 = Obscure 2 = Conspicuous | 1 | 1 |
| Rib Presence: 1 = Absent 2 = Present | 1 | 1 |
| No. Ribs per Fruit | N.A. | N.A. |
| Rib Width at Medial in mm | N.A. | N.A. |
| Ribs Surface: 1 = Smooth 2 = Netted | N.A. | N.A. |
| Suture Depth: 1 = Shallow (Golden Delight) 2 = Medium 3 = Deep (Hackensack) | N.A. | N.A. |
| Suture Surface: 1 = Smooth 2 = Netted | N.A. | N.A. |
| Shipping Quality: 1 = Poor (Home Garden) 2 = Fair (Short Distance Shipping) 3 = Excellent (Long Distance Shipping) | 2 | 2 |
| Fruit Abscission: 1 = When Ripe 2 = When Overripe 3 = Do Not Abscise | 3 | 3 |
| 7. RIND NET: | | |
| Net Presence: 1 = Absent 2 = Sparse 3 = Abundant | 1 | 1 |
| Distribution: 1 = Spotty 2 = Covers Entire Fruit | N.A. | N.A. |
| Coarseness: 1 = Fine 2 = Medium Coarse 3 = Very Coarse | N.A. | N.A. |
| Interlacing: 1 = None 2 = Some 3 = Complete | N.A. | N.A. |
| Interstices: 1 = Shallow 2 = Medium Deep 3 = Deep | N.A. | N.A. |
| 8. RIND TEXTURE: | | |
| Texture: 1 = Soft 2 = Firm 3 = Hard | 2 | 2 |
| Average Thickness at Medial in mm | 3.31 | 3.19 |
| 9. RIND COLOR: | | |
| Rind Color At Edible Maturity 01-white; 02 = cream; 03 = buff; 04 = yellow; 05 = gold; 06 = green; 07 = orange; 08 = bronze; 09 = brown; 10 = gray; 11 = black; 12 = other | | |
| Primary Color/Color Chart Value | 01 (RHS White 155A) | 04 (RHS Yellow orange 17C) |
| Mottling Color/Color Chart Value | N.A. | N.A. |
| Net Color/Color Chart Value | N.A. | N.A. |
| Furrow (Suture)/Color Chart Value | N.A. | N.A. |
| Rind Color At Full Maturity | | |
| Primary Color/Color Chart Value | 03 (RHS Yellow orange 16B) | 05 (RHS Yellow orange 17A) |
| Mottling Color/Color Chart Value | N.A. | N.A. |
| Net Color/Color Chart Value | N.A. | N.A. |
| Furrow (Suture)/Color Chart Value | N.A. | N.A. |
| 10. FLESH (At Edible Maturity): | | |
| Color Near Cavity/Color Chart Value | 01 (RHS White 155A) | 01 (RHS White 158B) |
| Color in Center/Color Chart Value | 01 (RHS White 155A) | 01 (RHS White 158B) |
| Color Near Rind/Color Chart Value | 01 (RHS White 155A) | 01 (RHS White 158B) |
| Refractometer % Soluable Solids (Center of Flesh) | 12.9 | 13.4 |
| Aroma: 1 = Absent 2 = Faint 3 = Strong | 1 | 1 |
| Flavor: 1 = Mild 2 = Somewhat Spicy 3 = Very Spicy | 1 | 1 |
| 11. SEED CAVITY: | | |
| Average Length in mm | 103.7 | 118.5 |
| Average Width in mm | 46.7 | 47.9 |
| Shape in X-Section: 1 = Circular 2 = Triangular | 1 | 2 |
| 12. SEEDS: | | |
| Average No. Seeds per Fruit | N.R. | N.R. |
| Average grams per 1,000 Seeds | N.R. | N.R. |

TABLE 2

| Non-USDA descriptor | Application Variety NUN 71504 MEM | Comparison Variety Reference variety |
|---|---|---|
| Petiole length of third leaf mature blade (mm) | 24.03 | 21.9 |
| Petiole diameter of third leaf mature blade (mm) | 8.49 | 8.11 |
| Peduncle length of fruit (mm) | 29.5 | 26.9 |
| Peduncle diameter of fruit (mm) | 7.4 | 7.5 |
| Blossom scar diameter of fruit at edible maturity (mm) | 9.83 | 9.53 |

Table 1 and 2 contain typical values. Values may vary due to environment. Other values that are substantially equivalent are also within the scope of the invention. N.A.=not applicable; n.r.=not recorded.

What is claimed is:

1. A plant, plant part or seed of melon variety NUN 71504 MEM, wherein a representative sample of said seed has been deposited under Accession Number NCIMB 43021.

2. The plant part of claim 1, further defined as a leaf, pollen, an ovule, a fruit, a scion, a rootstock, cutting, flower or a part of any of these or a cell.

3. A seed grown on the plant of claim 1.

4. A melon plant, or a part thereof which does not differ at the level of 5% from the plant of claim 2 in any of the characteristics of Table 1 and 2 when grown under the same environmental conditions.

5. A melon plant, or a part thereof which does not differ at the level of 5% from the plant of claim 1 when grown under the same environmental conditions.

6. A tissue or cell culture of regenerable cells of the plant of claim 1.

7. The tissue or cell culture according to claim 6, comprising cells or protoplasts from a plant part selected from the group consisting of embryos, meristems, cotyledons, hypocotyl, pollen, leaves, anthers, roots, root tips, pistil, petiole, flower, fruit, seed, stem and stalks.

8. A melon plant regenerated from the tissue or cell culture of claim 6, wherein the plant has all or all but one of the physiological and morphological characteristics of the plant of NUN 71504 MEM, wherein a representative sample of seed of said variety has been deposited under Accession Number NCIMB 43021, when determined at the 5% significance level for plants grown under the same environmental conditions.

9. A method of producing of the plant of claim 1, or a part thereof, comprising vegetative propagation of the plant of claim 1.

10. The method of claim 9, wherein said vegetative propagation comprises regenerating a whole plant from a part of the plant of claim 1.

11. The method of claim 9, wherein said part is a cutting, a cell culture or a tissue culture.

12. A vegetative propagated plant of claim 1, or a part thereof, wherein the plant has all of the physiological and morphological characteristics of the plant of claim 1 when grown under the same environmental conditions determined at the 5% significance level.

13. A method of producing a melon plant, comprising crossing the plant of claim 1 with a second melon plant one or more times, and selecting progeny from said crossing and optionally allowing the progeny to form seed.

14. A melon plant having one physiological and/or morphological characteristics which are different from those of the plant of claim 1 and which otherwise has all the physiological and morphological characteristics of the plant of claim 1 as listed in Table 1 and/or 2 and/or 3, when grown under the same environmental conditions determined at the 5% significance level.

15. A food or feed product comprising the plant part of claim 2 wherein the plant part can be identified as a part of the plant of the invention.

16. The plant of claim 1 further comprising a single locus conversion, wherein said plant has all or all but one of the morphological and physiological characteristics of the plant of claim 1 when grown under the same environmental conditions, optionally wherein the single locus conversion confers a trait selected from the group consisting of male sterility, herbicide tolerance, insect resistance, pest resistance, disease resistance, environmental stress tolerance, modified carbohydrate metabolism and modified protein metabolism.

17. A method of grafting a rootstock or scion of NUN 71504 MEM, said method comprising attaching tissue from the scion or rootstock of claim 2 to the tissue of a second plant, and optionally regenerating a plant therefrom.

18. A method of making doubled haploids of the plant of claim 1 comprising the step of making double haploid cells from haploid cells from the plant of claim 1 or a seed of claim 1.

19. A container comprising a plant, plant part or seed of claim 1.

* * * * *